United States Patent
Nanaumi

(10) Patent No.: US 8,875,582 B2
(45) Date of Patent: Nov. 4, 2014

(54) APPARATUS AND METHOD FOR PHOTOACOUSTIC IMAGING

(75) Inventor: Ryuichi Nanaumi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 288 days.

(21) Appl. No.: 13/051,632

(22) Filed: Mar. 18, 2011

(65) Prior Publication Data

US 2011/0232385 A1    Sep. 29, 2011

(30) Foreign Application Priority Data

Mar. 25, 2010   (JP) .................................. 2010-070326

(51) Int. Cl.
| | |
|---|---|
| *G01N 29/34* | (2006.01) |
| *G01N 29/44* | (2006.01) |
| *A61B 8/00* | (2006.01) |
| *A61B 5/00* | (2006.01) |

(52) U.S. Cl.
CPC ............. *A61B 5/0095* (2013.01); *A61B 5/4312* (2013.01)
USPC ................................ 73/602; 73/632; 600/437

(58) Field of Classification Search
USPC ........... 73/602–603, 606, 608, 587, 596, 632, 73/657; 600/407, 437, 473, 476–478
See application file for complete search history.

(56) References Cited

U.S. PATENT DOCUMENTS

| | | | | |
|---|---|---|---|---|
| 4,019,056 | A | * | 4/1977 | Block et al. .................... 250/344 |
| 4,666,308 | A | * | 5/1987 | Williams ....................... 356/432 |
| 4,690,284 | A | * | 9/1987 | Buckley et al. ............... 209/590 |
| 4,960,329 | A | * | 10/1990 | Schofield ..................... 356/5.09 |
| 5,384,573 | A | * | 1/1995 | Turpin ........................... 342/179 |
| 6,106,469 | A | | 8/2000 | Suzuki et al. |
| 6,289,230 | B1 | * | 9/2001 | Chaiken et al. ............... 600/322 |
| 6,709,393 | B2 | * | 3/2004 | Ogawa .......................... 600/443 |
| 6,979,292 | B2 | * | 12/2005 | Kanayama et al. ........... 600/437 |
| 7,079,257 | B1 | * | 7/2006 | Kirkpatrick et al. .......... 356/502 |
| 7,158,610 | B2 | * | 1/2007 | Mostafavi .................. 378/98.12 |
| 8,239,006 | B2 | * | 8/2012 | Zhu et al. ...................... 600/475 |
| 8,364,414 | B2 | * | 1/2013 | Masumura ...................... 702/19 |
| 2005/0187471 | A1 | * | 8/2005 | Kanayama et al. ........... 600/437 |
| 2009/0005685 | A1 | * | 1/2009 | Nagae et al. .................. 600/459 |
| 2011/0098550 | A1 | * | 4/2011 | Yoda ............................. 600/407 |
| 2011/0178401 | A1 | * | 7/2011 | Ichihara et al. ............... 600/437 |
| 2011/0208035 | A1 | * | 8/2011 | Baba et al. .................... 600/407 |
| 2011/0314921 | A1 | * | 12/2011 | Tsujita ........................... 73/657 |
| 2012/0157837 | A1 | * | 6/2012 | Nagata et al. ................. 600/437 |
| 2012/0179041 | A1 | * | 7/2012 | Nakagawa .................... 600/443 |

FOREIGN PATENT DOCUMENTS

JP           2000-107177 A       4/2000

* cited by examiner

*Primary Examiner* — Helen Kwok
(74) *Attorney, Agent, or Firm* — Canon USA Inc. IP Division

(57) ABSTRACT

A photoacoustic imaging apparatus includes a signal processor. The signal processor includes an adding unit configured to add received signals obtained by acoustic wave detecting devices to obtain a summed signal, a normalizing unit configured to normalize the summed signal for each acoustic wave detecting device with reference to an amplitude value in the received signal in the acoustic wave detecting device at the time when a maximum amplitude value in the summed signal is obtained to obtain a normalized signal, a reducing unit configured to subtract the normalized signal from the received signal for each acoustic wave detecting device to obtain a reduced signal in which the amplitude value in the received signal at the time when the maximum amplitude value in the summed signal is obtained is reduced, and an imaging unit configured to generate image data using the reduced signals.

15 Claims, 11 Drawing Sheets

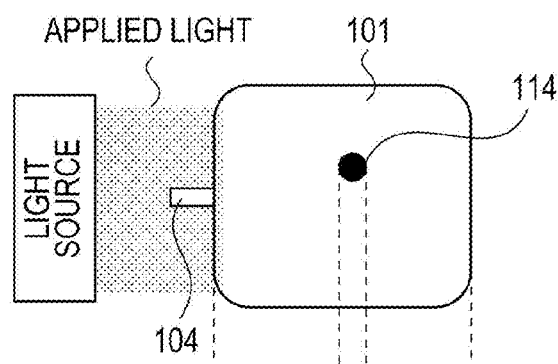
FIG. 1A
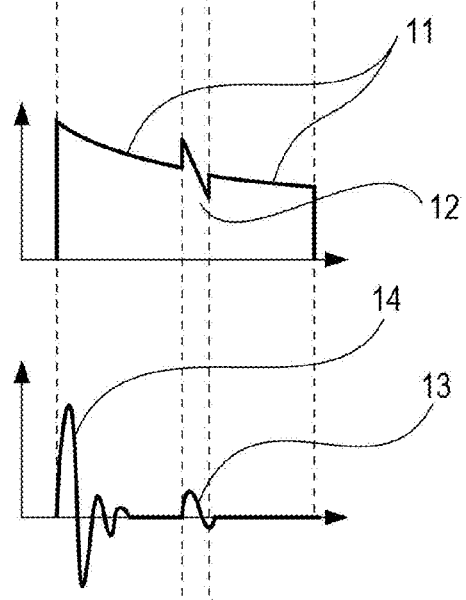
FIG. 1B
FIG. 1C
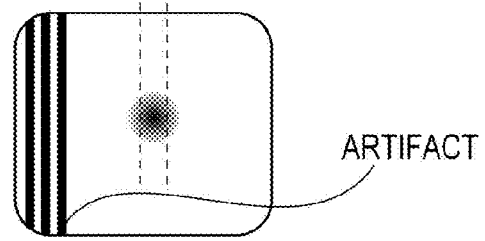
FIG. 1D

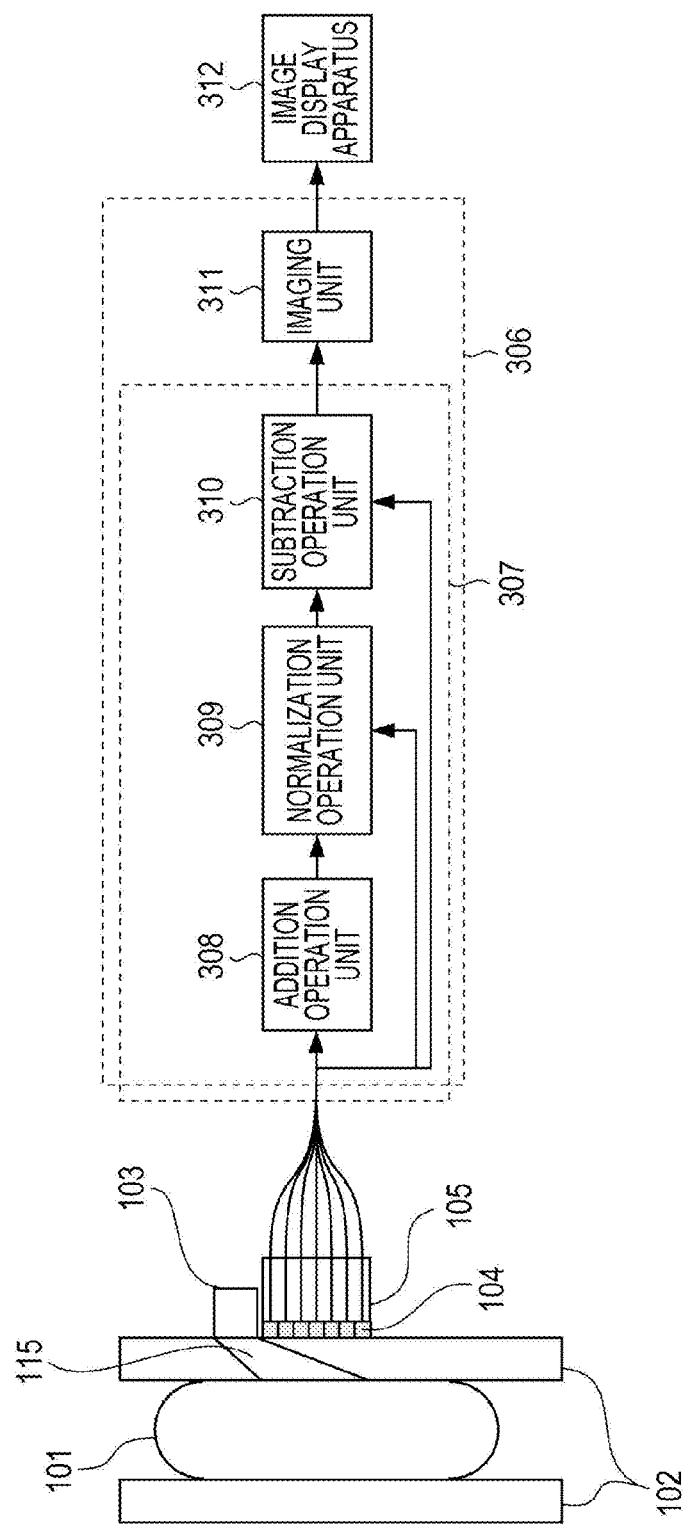

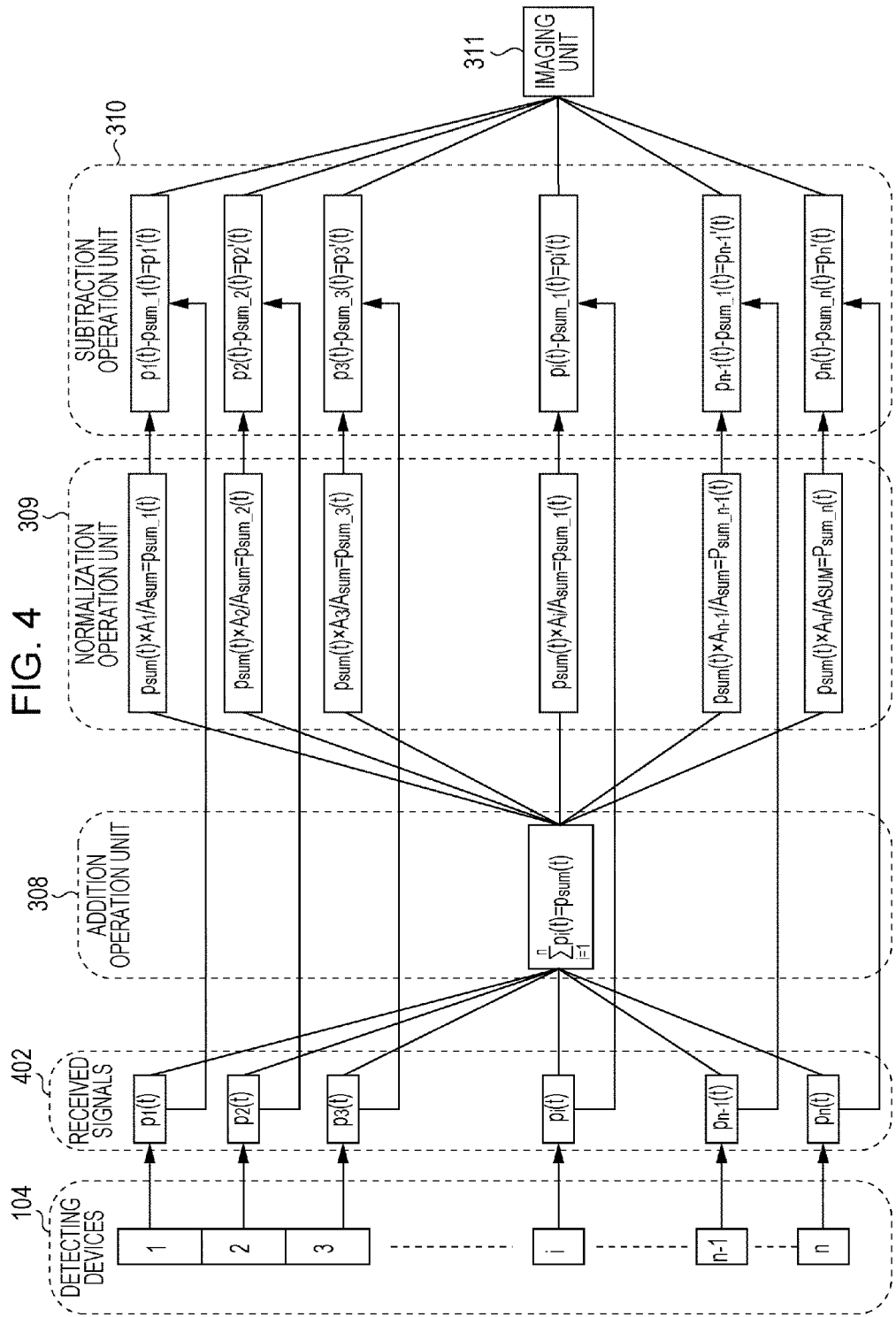

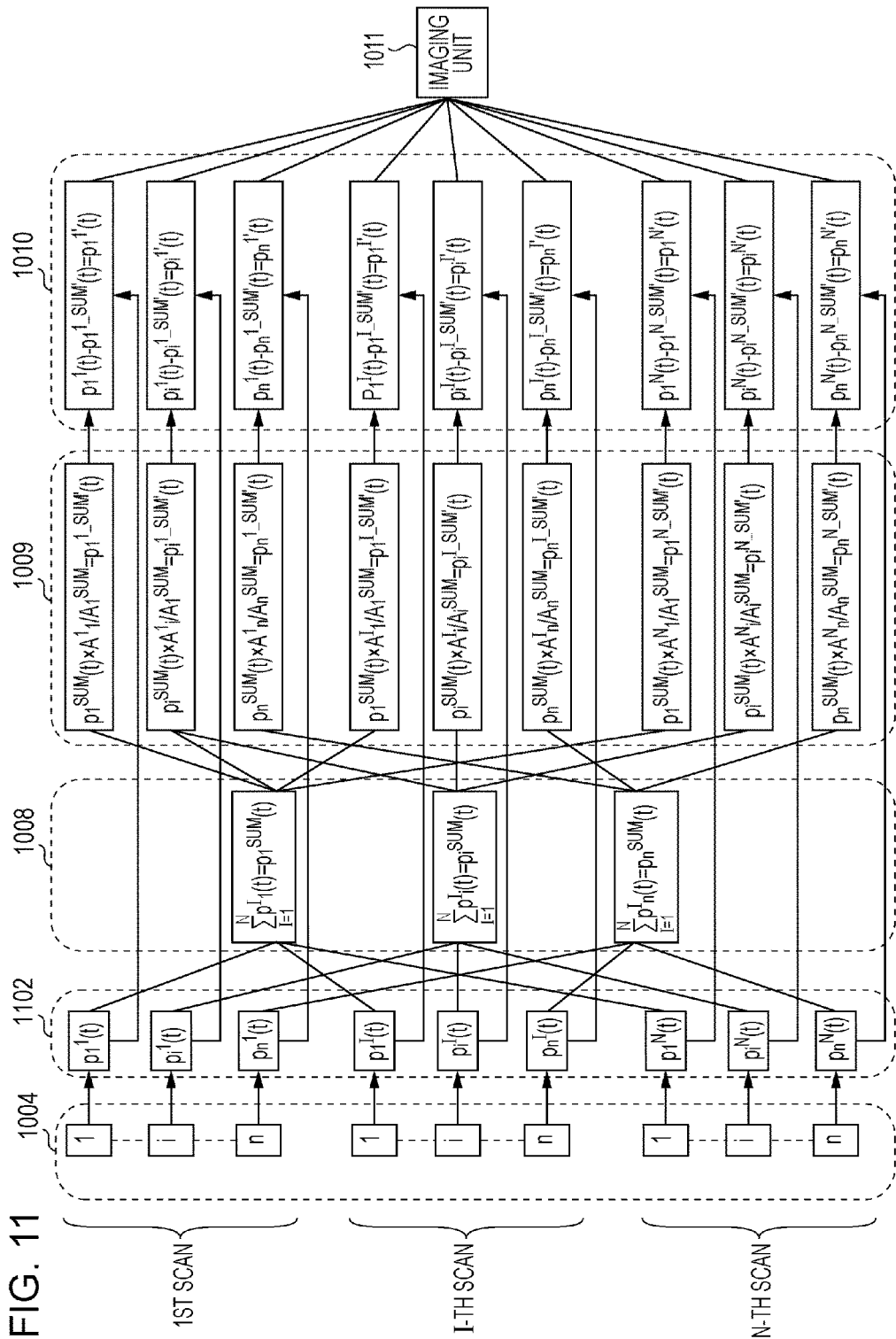

APPARATUS AND METHOD FOR PHOTOACOUSTIC IMAGING

BACKGROUND OF THE INVENTION

1. Field of the Invention

The present invention relates to an apparatus and method for photoacoustic imaging, and in particular, relates to a technique for measuring optical characteristics of the interior of a specimen using the photoacoustic effect.

2. Description of the Related Art

One of photoacoustic imaging techniques is photoacoustic tomography (PAT). According to the PAT technique, a specimen, such as biological tissue, is irradiated with pulsed light emitted from a light source. A light absorber absorbs the light propagated and scattered in the specimen, thus generating an acoustic wave. Such an acoustic wave generating mechanism is called the photoacoustic effect. A light absorber, such as tumor, often has a higher light energy absorption coefficient than its peripheral tissue. Accordingly, the light absorber absorbs more light than the peripheral tissue and instantaneously expands. In a photoacoustic imaging apparatus utilizing the photoacoustic effect, acoustic wave detecting devices receive an acoustic wave generated upon expansion, thus obtaining received signals. The received signals are mathematically analyzed, so that information about, for example, a distribution of sound pressure of the acoustic wave generated in the specimen can be imaged. A distribution of optical characteristic, particularly, absorption coefficient in the specimen can be obtained on the basis of image data obtained in this manner.

In PA imaging, light applied to a specimen may cause an acoustic wave (interfacial acoustic wave) on the surface (hereinafter, also referred to as "interface") of the specimen. The details will be described later. When the interfacial acoustic wave is received by an acoustic wave detecting device, a signal output from the acoustic wave detecting device includes a transient response caused by the limitation of a receivable frequency band of the detecting device. This transient response appears as an artifact in an image obtained by PA imaging. The artifact is an image which does not really exist but appears as if something exists there and is also called a ghost. If an acoustic wave caused by a light absorber reaches the acoustic wave detecting device after the interfacial acoustic wave, an image of the light absorber, such as tumor, may be hidden by the artifact. Alternatively, if a holding member, such as a plate, for fixing or holding a specimen is used upon acoustic wave measurement, an interfacial acoustic wave is reflected multiple times inside the holding member. Such a reflected wave (reflected interfacial acoustic wave) is also detected by the acoustic wave detecting device. Thus, the reflected interfacial acoustic wave also causes a transient response similar to the above described one. Disadvantageously, an image of a light absorber may be hidden by an artifact caused by the transient response.

The following problem is similar to the above-described problem caused by the reflected interfacial acoustic wave in the photoacoustic imaging apparatus. In an ultrasonic measuring apparatus using an ultrasonic echo, multiple reflections of a transmitted ultrasonic wave are repeated inside a member interposed between an acoustic wave detecting device and a specimen, thus causing artifacts. The artifacts caused by multiple echoes appear in an image.

A method of eliminating such artifacts caused by multiple echoes is disclosed in Japanese Patent Laid-Open No. 2000-107177. According to the method disclosed in Japanese Patent Laid-Open No. 2000-107177, an average signal obtained by averaging a plurality of received signals is subtracted from a received signal, thus eliminating an amplitude caused by multiple echoes.

Applied light generally has a spatial distribution of intensity. Thus, there is a difference in light intensity at different positions. The amplitude of an acoustic wave caused by the photoacoustic effect is proportional to the light intensity distribution. Accordingly, the above-described interfacial acoustic wave has a spatial distribution of sound pressure proportional to the spatial distribution of intensity of light applied to the interface of a specimen. Similarly, the reflected interfacial acoustic wave has a spatial distribution of sound pressure. The feature in which the spatial distribution of sound pressure is uneven is peculiar to the photoacoustic imaging apparatus having a feature in which the spatial distribution of light intensity is uneven.

In the photoacoustic imaging apparatus, an acoustic wave is received in different positions. Simultaneous reception of the acoustic wave in the different positions can reduce measurement time. Accordingly, a device array including acoustic wave detecting devices arranged one-dimensionally or two-dimensionally is generally used. Since the acoustic wave detecting devices receive an interfacial acoustic wave whose spatial distribution of sound pressure is uneven, the amplitude of the interfacial acoustic wave received differs from detecting device to detecting device. If the method disclosed in Japanese Patent Laid-Open No. 2000-107177 is used, a plurality of received signals having different amplitudes are averaged. An averaged amplitude caused by multiple echoes does not necessarily match an amplitude caused by multiple echoes in each received signal. Disadvantageously, if an average signal is subtracted from the received signal, the amplitude caused by multiple echoes is not sufficiently reduced in some cases. In other words, the method disclosed in Japanese Patent Laid-Open No. 2000-107177 is effective in the ultrasonic measuring apparatus in which a received signal amplitude caused by multiple echoes is constant. If the method is applied to the photoacoustic imaging apparatus in which the spatial distribution of sound pressure is uneven, it is difficult to achieve a satisfactory effect.

SUMMARY OF THE INVENTION

The present invention has been made in consideration of the above-described problems. The present invention provides a technique for obtaining image data with reduced artifacts by obtaining signals in each of which signal amplitudes caused by an interfacial acoustic wave and a reflected interfacial acoustic wave included in a received signal in PAT are reduced.

According to an aspect of the present invention, a photoacoustic imaging apparatus includes a plurality of acoustic wave detecting devices each configured to receive an acoustic wave generated in a specimen irradiated with light and convert the acoustic wave into a received signal, and a signal processor configured to generate image data using the received signals obtained by the acoustic wave detecting devices. The signal processor includes an adding unit configured to add amplitude values in the received signals obtained by the acoustic wave detecting devices at each time to obtain a summed signal, a normalizing unit configured to normalize the summed signal for each acoustic wave detecting device with reference to an amplitude value in the received signal of the acoustic wave detecting device at the time when a maximum amplitude value in the summed signal is obtained to obtain a normalized signal, a reducing unit configured to subtract the normalized signal from the received signal for each acoustic wave detecting device to obtain a reduced signal in which the amplitude value in the received signal at the time when the maximum amplitude value in the summed signal is obtained is reduced, and an imaging unit configured to generate image data using the reduced signals.

According to another aspect of the present invention, a photoacoustic imaging apparatus includes an irradiating unit configured to irradiate a specimen with light emitted from a light source, a plurality of acoustic wave detecting devices each configured to receive an acoustic wave generated in the specimen irradiated with the light and convert the acoustic wave into a received signal, a scanning unit configured to scan the acoustic wave detecting devices and the irradiating unit, and a signal processor configured to generate image data using the received signals obtained by the acoustic wave detecting devices. The light emitted from the light source is applied through the irradiating unit to the specimen in each scan position. The signal processor includes an adding unit configured to add amplitude values in the received signals obtained by the same acoustic wave detecting device at the different scan positions at each time when elapsed times from the time of irradiation with the light in the scan positions are equal, thus obtaining a summed signal for the acoustic wave detecting device, a normalizing unit configured to normalize the summed signal for each acoustic wave detecting device for each scan position with reference to an amplitude value in the received signal obtained by the acoustic wave detecting device in the scan position at the time when a maximum amplitude value in the summed signal for the acoustic wave detecting device is obtained, thus obtaining a normalized signal, a reducing unit configured to subtract the normalized signal from the received signal for each acoustic wave detecting device in each scan position to obtain a reduced signal in which the amplitude value in the received signal obtained by the acoustic wave detecting device in the scan position at the time when the maximum amplitude value in the summed signal is obtained is reduced, and an imaging unit configured to generate image data using the reduced signals.

According to the present invention, signals in each of which signal amplitudes caused by an interfacial acoustic wave and a reflected interfacial acoustic wave included in a received signal in PAT are reduced are obtained, thus reducing artifacts in an image.

Further features of the present invention will become apparent from the following description of exemplary embodiments with reference to the attached drawings.

BRIEF DESCRIPTION OF THE DRAWINGS

FIGS. 1A to 1D are schematic diagrams explaining a mechanism to cause an artifact.

FIG. 3 is a schematic diagram illustrating a photoacoustic imaging apparatus according to a first embodiment of the present invention.

FIG. 4 is a signal flow diagram in a signal processor in the first embodiment.

FIG. 11 is a signal flow diagram in a signal processor in the second embodiment.

DESCRIPTION OF THE EMBODIMENTS

Figure 2A:
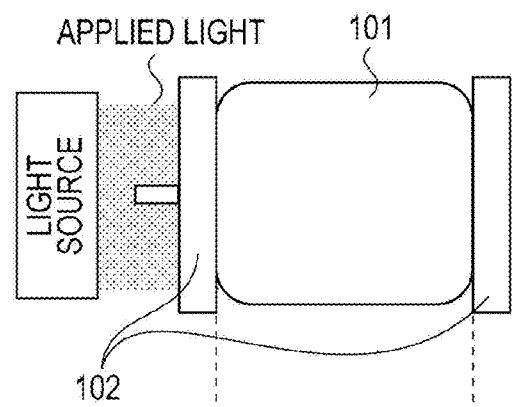
FIGS. 2A to 2C illustrate the schematic configuration of a photoacoustic imaging apparatus including holding plates and schematically illustrate artifacts.

In the specification of the present invention, acoustic waves include waves called acoustic waves, ultrasonic waves, and photoacoustic waves and mean elastic waves generated when a specimen is irradiated with light (electromagnetic wave), such as near infrared radiation. In addition, an acoustic wave generated on the surface of a specimen or the surface of an acoustic wave detecting device is called an "interfacial acoustic wave" and multiple reflection of the interfacial acoustic wave by, for example, a holding member is called a "reflected interfacial acoustic wave".

First, an interfacial acoustic wave and a transient response will be described in detail. FIG. 1A is a schematic diagram illustrating a state in which acoustic waves are received in use of PAT. FIG. 1B illustrates the waveform of sound pressures of acoustic waves reached an acoustic wave detecting device plotted against time. Reference numeral 11 denotes the sound pressure of an acoustic wave (including an interfacial acoustic wave) generated due to light absorption by a specimen 101 (including the surface thereof). Reference numeral 12 denotes the sound pressure of an acoustic wave generated by a light absorber 114, such as tumor, existing locally in the specimen. If the acoustic wave detecting device is placed on the light radiation side, light reflected by the specimen impinges on the surface of the acoustic wave detecting device, so that an acoustic wave may be generated from the surface of the acoustic wave detecting device (such a state is not illustrated). In the specification of the present invention, interfacial acoustic waves include not only an interfacial acoustic wave generated from the surface of a specimen but also an interfacial acoustic wave generated from the surface of an acoustic wave detecting device. FIG. 1C illustrates the waveform of a received signal output from the acoustic wave detecting device, indicated at 104, plotted against time. Reference numeral 14 denotes a transient response (amplitude) caused by an interfacial acoustic wave generated in an interface position of the specimen. The transient response is caused because the frequency band of acoustic waves receivable by the acoustic wave detecting device is limited. FIG. 1D is a schematic diagram of an image based on the received signal. The transient response appears as an artifact, as illustrated in FIG. 1D. If the light absorber, such as tumor, is closer to the acoustic wave detecting device than the arrangement in FIG. 1A, an amplitude 13 caused by the light absorber may be hidden by the amplitude 14, serving as the transient response, caused by the interfacial acoustic wave and an image of the light absorber may be hidden by the artifact.

Figure 2B:
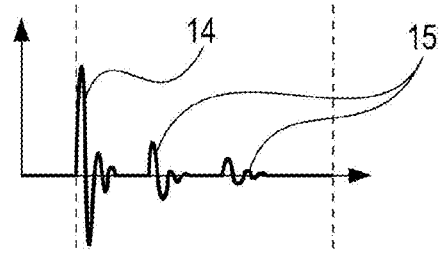

Next, a reflected interfacial acoustic wave will be described in detail. In some cases, such a photoacoustic imaging apparatus includes holding members, e.g., holding plates, for holding a specimen as illustrated in FIG. 2A. When the apparatus includes the holding plates as illustrated in FIG. 2A, an interfacial acoustic wave is reflected multiple times inside the holding plates, so that such a reflected wave (reflected interfacial acoustic wave) is also received by the acoustic wave detecting device. The reflected interfacial acoustic wave appears as amplitudes 15 caused by the reflected interfacial acoustic wave in a received signal as illustrated in FIG. 2B. Specifically, the amplitude 14 is caused when the interfacial acoustic wave, generated on the interface between the specimen and the holding plate, is propagated through the holding plate and is received by the acoustic wave detecting device. The amplitudes 15 are caused when the interfacial acoustic wave is reflected by the surface of the holding plate adjacent to a light source and is then reflected by the surface (interface) thereof adjacent to the specimen and is then received by the acoustic wave detecting device.

Figure 2C:
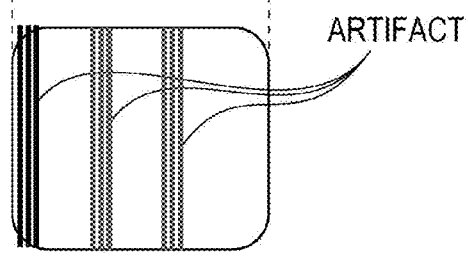

FIG. 2C is a schematic diagram of an image based on the received signals. If an image is obtained from the received signals including amplitudes caused by the reflected interfacial acoustic wave, an image of tumor or the like may be hidden by artifacts caused by the reflected interfacial acoustic wave in a manner similar to the case related to the interfacial acoustic wave.

In the following embodiments, the configurations of apparatuses and methods for reducing artifacts generated by amplitudes caused by an interfacial acoustic wave and a reflected interfacial acoustic wave will be described. Preferred exemplary embodiments of the present invention will be described in detail with reference to the drawings.

First Embodiment

According to a first embodiment of the present invention, received signals output from acoustic wave detecting devices arranged in an array are added to obtain a summed signal and the summed signal is normalized for each acoustic wave detecting device. The normalized signals and the received signals are used to reduce signal amplitudes caused by an interfacial acoustic wave and a reflected interfacial acoustic wave.

Configuration of Apparatus

FIG. 3 schematically illustrates a photoacoustic imaging apparatus according to the first embodiment of the present invention. In the photoacoustic imaging apparatus, a light source emits light (pulsed light) and the specimen 101 is irradiated with the light, indicated at 115, through an irradiating unit 103. A light absorber (e.g., tumor to be detected) in the specimen 101 absorbs light energy, thus generating an acoustic wave. The generated acoustic wave is propagated through the specimen and then reaches the acoustic wave detecting devices 104 through a holding plate, serving as a holding member. An interfacial acoustic wave is also generated by the surface of the specimen or the surfaces of the acoustic wave detecting devices and the generated wave reaches the acoustic wave detecting devices 104. The acoustic wave detecting devices 104 receive the acoustic wave and the interfacial acoustic wave, convert the waves into electrical signals (received signals), and output the signals to a signal processor 306. In the signal processor 306, the received signals are subjected to, for example, amplification and digital conversion. After that, the digitally converted received signals are transmitted to an addition operation unit (adding unit) 308. A signal output from the addition operation unit 308 is transmitted to a normalization operation unit (normalizing unit) 309. Signals normalized by the normalization operation unit 309 are transmitted to a subtraction operation unit (reducing unit) 310. The addition operation unit 308, the normalization operation unit 309, and the subtraction operation unit 310 constitute an interfacial acoustic wave reducer 307. This interfacial acoustic wave reducer 307 reduces signal amplitudes caused by the interfacial acoustic wave and the reflected interfacial acoustic wave from the received signals. The details of processes performed by each unit will be described later. Signals output from the interfacial acoustic wave reducer 307 are input to an imaging unit 311. The imaging unit 311 generates image data on the basis of the input signals (image reconstruction). The generated image data is output to an image display apparatus 312, so that an image based on the data is displayed.

The light source according to the embodiment of the present invention includes at least one of a coherent pulsed light source and an incoherent pulsed light source. In order to achieve the photoacoustic effect, the width of a pulse is preferably several hundreds of nanoseconds or less and, more preferably, in the range of 5 to 50 nanoseconds. To determine whether breast cancer is present, the light source emits light having a specific wavelength absorbed by a specific component (e.g., hemoglobin) of components of biological tissue. As a light source, a laser having high power output can be used. A light-emitting diode may be used instead of the laser. Various lasers, such as a solid-state laser, a gas laser, a dye laser, and a semiconductor laser, can be used.

Since the sound pressure of an acoustic wave is proportional to light intensity, not only one side surface of a specimen but also surfaces thereof can be irradiated with light in order to increase the S/N (signal-to-noise) ratio of received signals. In particular, when a specimen 101 is sandwiched by the holding plates 102 as illustrated in FIG. 3, the specimen may be irradiated with light such that light is applied to the specimen from each of the surfaces of the holding plates (on the side adjacent to the acoustic wave detecting devices and the opposite side).

The irradiating unit 103 is an optical member for guiding light emitted from the light source to the specimen and applying the light to the specimen. The irradiating unit 103 includes, for example, a mirror reflecting light, a lens changing the shape of light, for example, converging or diverging the light, a prism scattering, deflecting, or reflecting the light, or an optical fiber. Any optical member other than the above members may be used so long as the member can apply light emitted from the light source to the specimen so that the light has a desired shape. An area irradiated with light (hereinafter, referred to as "light-irradiated area") may be moved in the specimen. In other words, light emitted from the light source is movable on the specimen. If emitted light is movable, a wider range can be irradiated with light. The light-irradiated area in the specimen (light applied to the specimen) may be moved synchronously with the acoustic wave detecting devices. According to a method of moving the light-irradiated area in the specimen, the irradiating unit can be mechanically moved synchronously with the acoustic wave detecting devices. If the light source is small, the light source itself may be mechanically moved.

The holding plates, indicated at 102, serve as members for keeping at least part of the specimen in a constant shape. Referring to FIG. 3, when one holding plate 102 is urged against at least one side of the specimen such that the specimen is sandwiched between the holding plates 102, the position of the specimen is fixed during measurement, thus preventing a position error caused by, for example, movement of a human body. In addition, pressing the specimen from both sides thereof by the holding plates 102 allows light to efficiently reach deeper part of the specimen. As for a material for the holding members, a high light-transmissive material highly acoustically matching with the specimen 101 and the acoustic wave detecting devices 104 can be used. To increase the acoustic matching, an acoustic matching member, such as gel, may be interposed between each holding plate 102 and the specimen 101 or between the holding plate 102 and the acoustic wave detecting devices 104.

The acoustic wave detecting devices 104 each convert an acoustic wave into a received signal, serving as an electrical signal, and each include a transducer using a piezoelectric phenomenon, a transducer using resonance of light, or a transducer using a change in capacity. Any acoustic wave detecting device may be used so long as the device can receive an acoustic wave and convert the wave into an electrical signal. In the present embodiment of the present invention, the device array, indicated at 105, including the acoustic wave detecting devices arranged one-dimensionally or two-dimensionally is used. An acoustic wave is received by the acoustic wave detecting devices, each acoustic wave detecting device outputs a received signal, and each received signal is supplied to the signal processor 306.

The signal processor 306 includes the interfacial acoustic wave reducer 307 and the imaging unit 311. The signal processor 306 may be a program installed on a computer or an electronic circuit. The imaging unit 311 generates image data (or reconstructs an image) using backprojection in the time domain or Fourier domain generally used in tomography technology. In the embodiment, whether two-dimensional or three-dimensional, image data is data indicating information about the interior of a specimen (e.g., biological information about the distribution of initial sound pressure or light absorption coefficient in biological tissue). When image data is two-dimensional, the data includes pixel data items arranged. When image data is three-dimensional, the data includes voxel data items arranged.

The details of processes and procedures of the units included in the interfacial acoustic wave reducer 307 will be described below.

Processes

The processes in the signal processor 306 in FIG. 3 will be described with reference to FIGS. 4 and 5A to 5E.

Referring to FIG. 4, n acoustic wave detecting devices 104 receive an acoustic wave, thus obtaining received signals 402. The received signal output from each acoustic wave detecting device is a time-series signal. Let $p_i(t)$ denote a received signal obtained by the i-th acoustic wave detecting device 104.

Figure 5A:
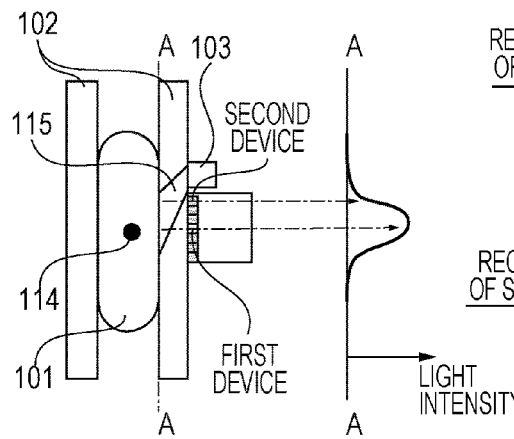
FIGS. 5A to 5E schematically illustrate a mechanism to reduce signal amplitudes caused by an interfacial acoustic wave and a reflected interfacial acoustic wave.
Figure 5B:
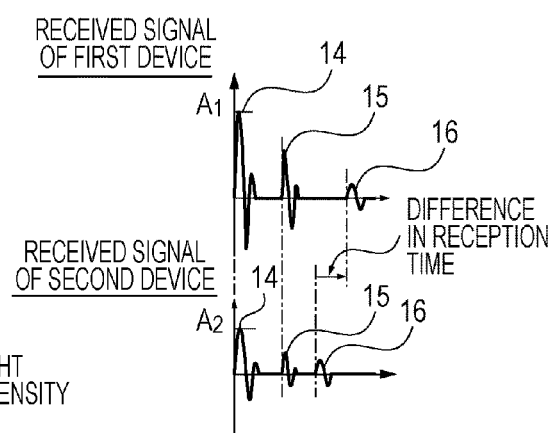

The received signals obtained by the acoustic wave detecting devices will now be described with reference to FIGS. 5A and 5B. FIG. 5A illustrates the spatial distribution of light intensity in a cross section taken along the line A-A. FIG. 5B illustrates the waveforms of received signals plotted against time, the signals being obtained in the spatial distribution of light intensity in FIG. 5A. In FIG. 5B, upper part illustrates the waveform of a received signal, obtained by a first device (the acoustic wave detecting device positioned in the middle in FIG. 5A), plotted against time and lower part illustrates that obtained by a second device (the acoustic wave detecting device positioned at the top in FIG. 5A). Referring to FIG. 5B, the two devices differ from each other in the time (i.e., reception time at which an acoustic wave generated by the light absorber is received) when an amplitude 16 caused by an acoustic wave generated by the light absorber appears. The reason is that the acoustic wave generated by the light absorber is a spherical wave and the distance from the light absorber to the first device differs from that to the second device, namely, the two devices differ from each other in the time when the acoustic wave reaches the device. On the other hand, the time when the amplitude 14 caused by an interfacial acoustic wave appears and the time when the amplitude 15 caused by a reflected interfacial acoustic wave appears, namely, reception times of the interfacial acoustic wave and the reflected interfacial acoustic wave in the first device coincide with those in the second device. Since the speed of light is several orders of magnitude higher than the speed of sound, applied light can be regarded as it reaches all positions at the same time regardless of distance. In other words, since the time when an interfacial acoustic wave is generated on the surface of a specimen is the same, the interfacial acoustic wave is a plane wave. Since the distance from the interface of the specimen to the first device is the same as that to the second device, the reception times of the interfacial acoustic wave and the reflected interfacial acoustic wave in the first device are the same as those in the second device.

As illustrated in FIG. 5B, however, the magnitude (amplitude value) of the amplitude 14 caused by the interfacial acoustic wave and that of the amplitude 15 caused by the reflected interfacial acoustic wave in the first device differ from those in the second device. In other words, when let $A_1$ denote the amplitude value caused by the interfacial acoustic wave in the received signal of the first device and let $A_2$ denote the amplitude value caused by the interfacial acoustic wave in the received signal of the second device, $A_1 \neq A_2$. The reason is that the spatial distribution of intensity of light applied to the specimen is uneven as illustrated in FIG. 5A. Specifically, since the light intensity in front of the first device is high, the amplitude value $A_1$ is high. Since the light intensity in front of the second device is low, the amplitude value $A_2$ is low. The reflected interfacial acoustic wave attenuates at a constant rate relative to the interfacial acoustic wave. Accordingly, a ratio of the amplitude 14 caused by the interfacial acoustic wave to the amplitude 15 caused by the reflected interfacial acoustic wave in the first device can be regarded as the same as that in the second device.

Figures 5C, 5D:
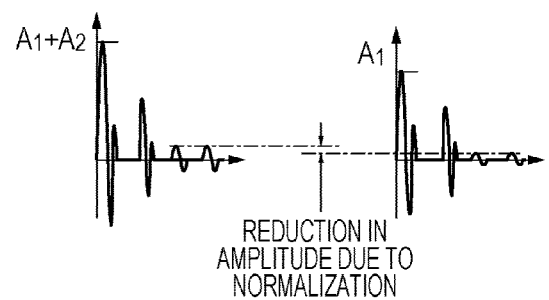

A process (adding step) in the addition operation unit 308 will be described below. The addition operation unit 308 adds the received signals obtained by the acoustic wave detecting devices at each time (at the same time). Specifically, amplitude values of the received signals at each time are added. Referring to FIG. 4, a summed signal $p_{sum}(t)$ is obtained by adding the received signals in the addition operation unit 308. FIG. 5C illustrates the waveform of the summed signal plotted against time, the signal being obtained by adding received signals of the first and second devices for the convenience of description. In the summed signal, the amplitudes caused by the interfacial acoustic wave at the same reception time are added and the amplitudes caused by the reflected interfacial acoustic wave at the same reception time are added. In other words, an amplitude value caused by the interfacial acoustic wave at the reception time is expressed by $A_1+A_2$. However, amplitudes caused by the acoustic wave generated from the light absorber at different reception times are not added.

In the normalization operation unit 309 (normalizing step), the above-described summed signal is normalized for each acoustic wave detecting device. Referring to FIG. 4, $A_{sum}$ indicates a maximum amplitude value included in the summed signal $p_{sum}(t)$ and $A_i$ indicates an amplitude value in the received signal $p_i(t)$ at the time when the maximum amplitude value $A_{sum}$ is obtained. In the normalization operation unit 309, the summed signal $p_{sum}(t)$ is normalized for each acoustic wave detecting device with reference to the amplitude value $A_i$ in the received signal $p_i(t)$ at the time when the maximum amplitude value $A_{sum}$ is obtained in the summed signal $p_{sum}(t)$, thus obtaining a normalized signal $p_{sum\_i}(t)$. Specifically, for the i-th device, the summed signal $p_{sum}(t)$ may be multiplied by a ratio of the amplitude value $A_i$ to the maximum amplitude value $A_{sum}$. This process will be described in more detail with reference to FIG. 5D. FIG. 5D illustrates the waveform of a normalized signal for the first device plotted against time. Since the maximum amplitude value of the summed signal is $A_1+A_2$ with reference to FIG.

5C, an amplitude value in the received signal at the time (temporarily indicated at t1) when the maximum amplitude value $A_1+A_2$ is obtained is $A_1$. In other words, the summed signal is multiplied by $A_1/(A_1+A_2)$, thus normalizing the summed signal. Consequently, the normalized signal is obtained. An amplitude value in the normalized signal at time t1 is $A_1$ and matches the amplitude value in the received signal at time t1. As for an amplitude caused by the reflected interfacial acoustic wave, an amplitude value in the normalized signal matches that in the received signal (because the reflected interfacial acoustic wave attenuates at a constant rate relative to the interfacial acoustic wave). On the other hand, the amplitudes caused by the acoustic wave generated from the light absorber are remarkably reduced (to approximately zero) as compared with the amplitudes in the received signals at the same times. To obtain a normalized signal for the second device, the summed signal may be multiplied by $A_2/(A_1+A_2)$. In this manner, the interfacial acoustic wave and the reflected interfacial acoustic wave can be extracted.

Figure 5E:
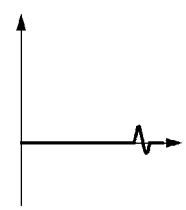

A process (reducing step) in the subtraction operation unit 310 will now be described. Referring to FIG. 4, $p_i'(t)$ denotes a reduced signal in which a ratio of an amplitude caused by the interfacial acoustic wave to an amplitude caused by the light absorber and a ratio of an amplitude caused by the reflected interfacial acoustic wave to an amplitude caused by the light absorber are reduced as compared with those in the received signal. In the subtraction operation unit 310, an amplitude caused by the interfacial acoustic wave and that caused by the reflected interfacial acoustic wave are reduced in a received signal of each acoustic wave detecting device on the basis of the normalized signal for the acoustic wave detecting device obtained in the normalizing step. Specifically, the normalized signal is subtracted from the received signal for each acoustic wave detecting device. In other words, an amplitude value in the normalized signal at each time is subtracted from that in the received signal at the same time. As for the amplitude caused by the interfacial acoustic wave and that caused by the reflected interfacial acoustic wave, since their amplitude values in the normalized signal match those in the received signal, the normalized signal is subtracted from the received signal, thus reducing the amplitudes caused by the interfacial acoustic wave and the reflected interfacial acoustic wave (to zero in theory). On the other hand, the amplitude caused by the light absorber in the normalized signal is approximately zero. Accordingly, if the normalized signal is subtracted from the received signal, the amplitude caused by the light absorber is hardly reduced. FIG. 5E illustrates the waveform of a reduced signal for the first device. It can be seen in FIG. 5E that the amplitude caused by the interfacial acoustic wave and that caused by the reflected interfacial acoustic wave are eliminated and the amplitude caused by the light absorber becomes apparent. As for a reduced signal for the second device, a normalized signal for the second device may be subtracted from the received signal of the second device.

The reduced signals are output to the imaging unit 311. The imaging unit 311 generates image data using the reduced signals. When image data is generated using reduced signals as described above, artifacts caused by an interfacial acoustic wave and a reflected interfacial acoustic wave in an image are reduced as compared with a case where image data is generated directly from received signals (i.e., a case where the present invention is not applied).

In the present embodiment, the assumption using two acoustic wave detecting devices has been described for the convenience of description using FIGS. 5A to 5E. Actually, the effect of reducing an amplitude caused by an interfacial acoustic wave and that caused by a reflected interfacial acoustic wave can be enhanced using more received signals. In the embodiment of the present invention, methods of obtaining a normalized signal and a reduced signal for each acoustic wave detecting device are not limited to the above-described operation methods. As another method for normalization, for example, the summed signal $p_{sum}(t)$ may be divided by the amplitude value $A_i$ in the received signal at the time when the maximum amplitude value $A_{sum}$ is obtained. Explanation will be made on the assumption that two received signals are used. Regarding the first device, the summed signal is divided by the amplitude value $A_1$. In other words, the amplitude in the normalized signal at time t1 is expressed by $(A_1+A_2)/A_1$. In this case, in the reducing step, the received signal is multiplied by $(A_1+A_2)/A_1^2$ and the normalized signal is subtracted from the resultant received signal, so that the amplitude caused by the interfacial acoustic wave and that caused by the reflected interfacial acoustic wave can be reduced (to zero in theory). In the embodiment of the present invention, after the received signal is multiplied by $(A_1+A_2)/A_1^2$, the resultant signal is called "received signal" for the sake of convenience. Specifically, the subtraction of the normalized signal from the received signal at time t1 is expressed as $A_1 \times (A_1+A_2)/A_1^2 - (A_1+A_2)/A_1 = 0$. After that, the obtained reduced signal may be multiplied by $A_1^2/(A_1+A_2)$.

As for the method of obtaining a normalized signal, any operation method may be used so long as the summed signal is normalized for each acoustic wave detecting device with reference to an amplitude in the received signal at the time when the maximum amplitude value is obtained. As for the method of obtaining a received signal, any operation method can be used so long as a received signal is processed in consideration of the operation method for normalization and, after that, an amplitude in the received signal at the time when the maximum amplitude value is obtained is reduced.

In FIG. 4, the received signals of all the acoustic wave detecting devices are added to obtain the summed signal in the present embodiment. However, it is unnecessary to add all of the received signals. Received signals by which the effect of reducing an interfacial acoustic wave and a reflected interfacial acoustic wave can be sufficiently obtained may be selected to obtain a summed signal.

Example 1

Figure 6:
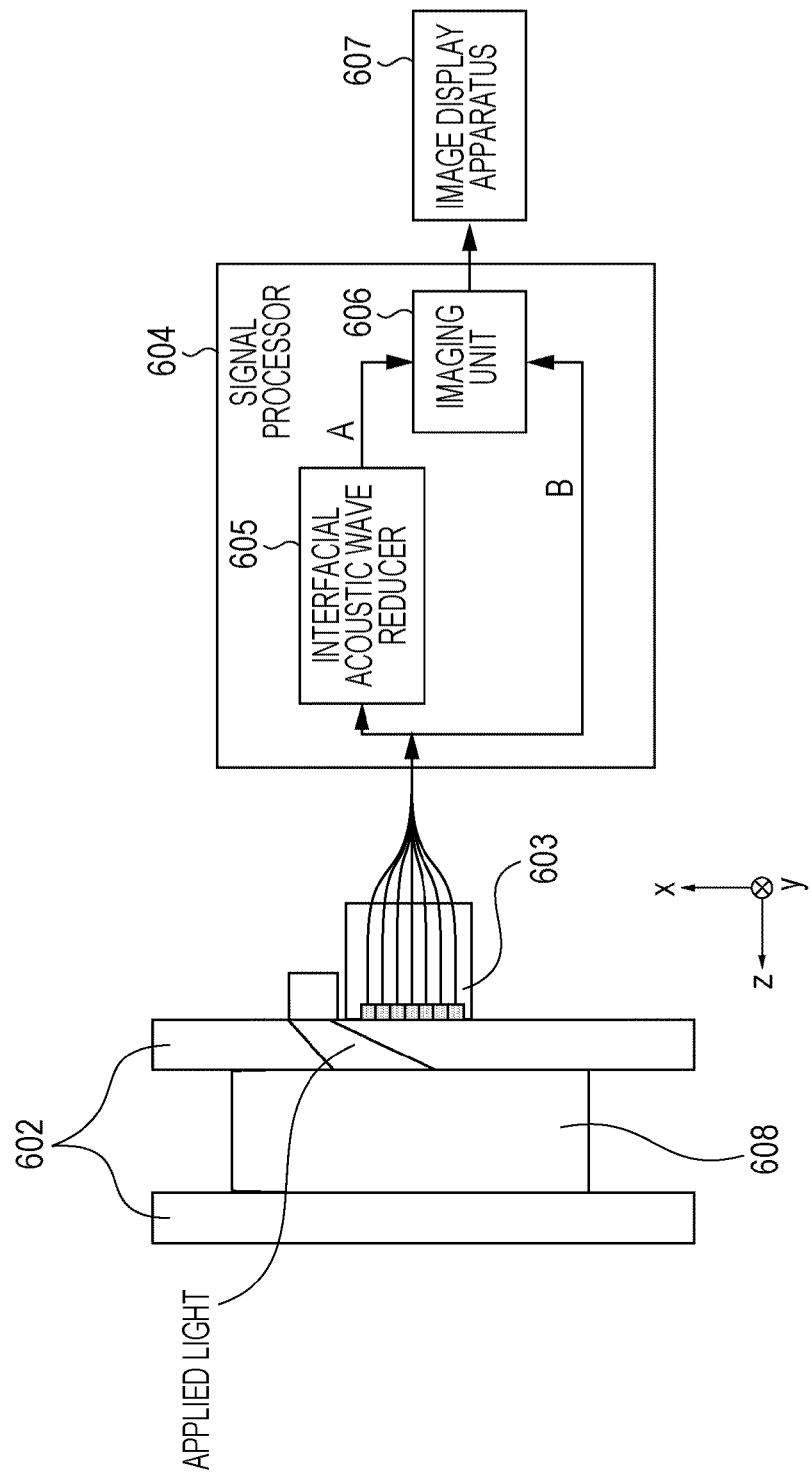
FIG. 6 is a schematic diagram illustrating a photoacoustic imaging apparatus according to an application of the first embodiment.
Figure 7:
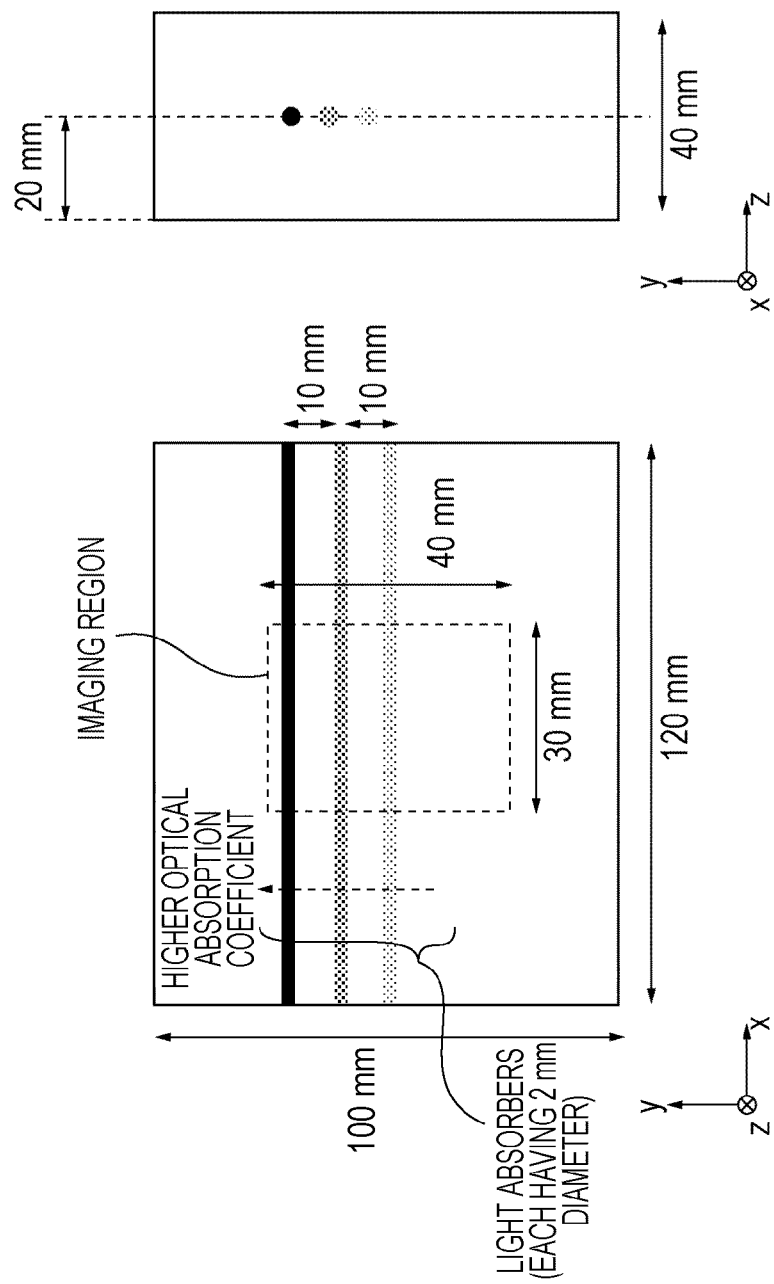
FIG. 7 schematically illustrates a phantom used for measurement.

An example in which image data was actually generated according to an application of the first embodiment will be described below. FIG. 6 schematically illustrates a photoacoustic imaging apparatus used. A Nd:YAG laser generating pulsed light of approximately 10 nanoseconds (FWHM) and having a wavelength of 1064 nm was used as a light source. Plastic plates having a thickness of 10 mm were used as holding plates 602. A device array 603 included devices of lead zirconate titanate (PZT) arranged two-dimensionally. The number of devices was 18×18, the arrangement of devices was a square type (square matrix), and the pitch of devices was 2 mm. A signal processor 604 included an interfacial acoustic wave reducer 605 and an imaging unit 606 and was installed as a program on a computer. Signal flows in the signal processor 604 included a flow A and a flow B. In the flow A, received signals were supplied from the device array 603 to the interfacial acoustic wave reducer 605 and reduced signals were supplied from the interfacial acoustic wave reducer 605 to the imaging unit 606. In the flow B, received signals were directly supplied from the device array 603 to the imaging unit 606. The interfacial acoustic wave reducer 605 is the same as the interfacial acoustic wave reducer 307 in FIG. 3. The imaging unit 606 is the same as the imaging unit 311 in FIG. 3. An image display apparatus 607 displayed image data generated by the signal processor as an image. In this example, a phantom 608, serving as a urethane biological tissue model, was used as a specimen. The phantom 608 has optical characteristics and acoustic characteristics approximate to those of biological tissue. FIG. 7 illustrates the configuration of the phantom 608. A coordinate system in FIG. 7 coincides with that in FIG. 6.

Referring to FIG. 7, in the phantom 608, rod-shaped light absorbers having higher optical absorption coefficients than that of the phantom were buried. The light absorbers had different optical absorption coefficients. When the phantom was irradiated with light, acoustic waves were generated from the light absorbers. The device array detected the propagated acoustic waves to obtain received signals. The signal processor 604 generated image data representing the light absorbers in the phantom 608 using the received signals. An image was displayed on the image display apparatus 607.

Figure 8:
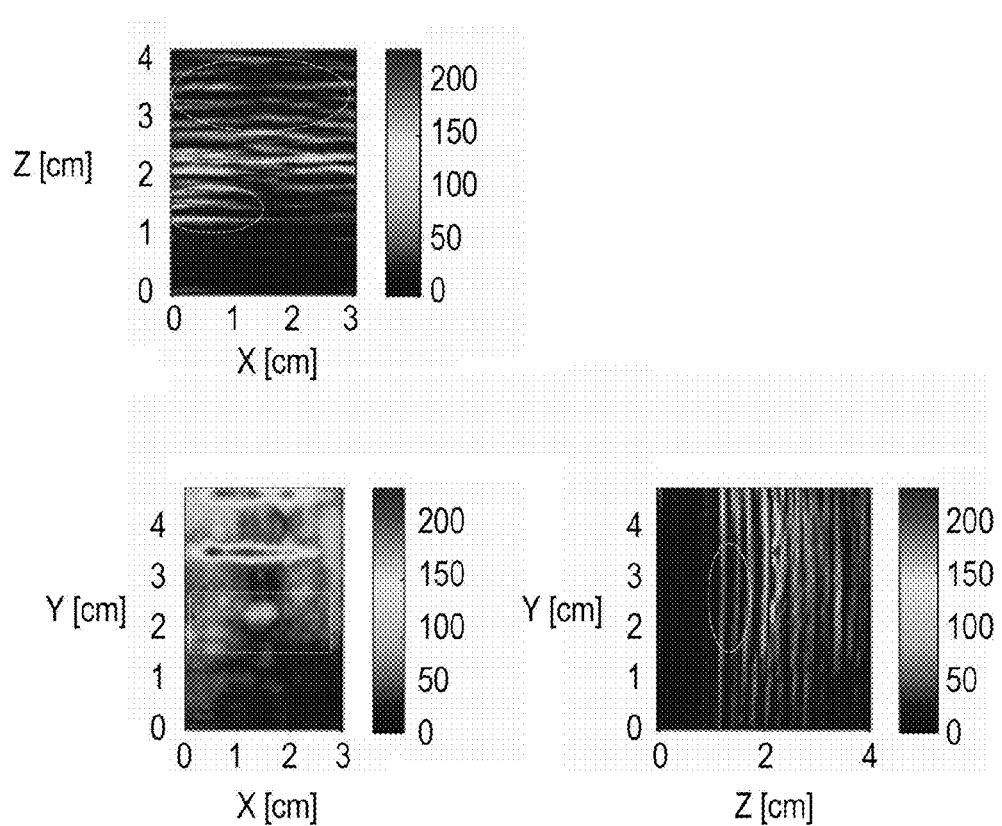
FIG. 8 illustrates images obtained when the present invention was not applied.
Figure 9:
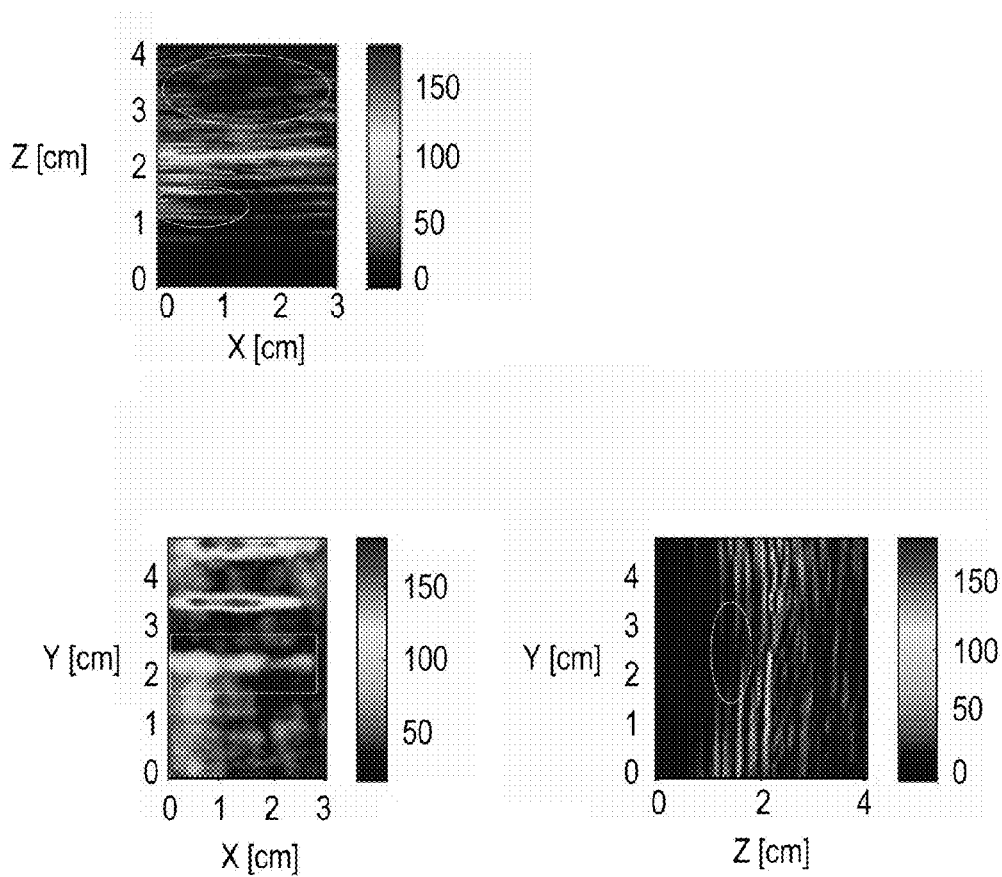
FIG. 9 illustrates images obtained when the first embodiment was applied.

FIG. 8 illustrates images (comparative examples) of the phantom 608 obtained in the flow B in FIG. 6. The images of FIG. 8 are maximum-intensity-projection (MIP) images each obtained by projecting the highest sound pressure values of acoustic waves in a certain coordinate axis to a plane orthogonal to the coordinate axis in the coordinate system in FIG. 6. FIG. 9 illustrates images of the phantom 608 obtained in the flow A in FIG. 6. The images of FIG. 9 are MIP images in the coordinate system in FIG. 6.

When the MIP images of FIG. 8 are compared to those of FIG. 9, it can be seen that reflected interfacial acoustic waves recognized in ovals in FIG. 8 were reduced in FIG. 9. The reduction of the reflected interfacial acoustic waves allows the images of the light absorbers to become more apparent relatively. Accordingly, it can be seen that the light absorbers in a rectangle were not imaged in FIG. 8 but the light absorbers in a rectangle were imaged in FIG. 9.

As described above, the photoacoustic imaging apparatus according to the application of the first embodiment can reduce interfacial acoustic waves, thus reducing artifacts.

Second Embodiment

A photoacoustic imaging apparatus according to a second embodiment further includes a scanning unit that scans acoustic wave detecting devices and a light-irradiated area (irradiating unit) relative to a specimen. In an adding step, received signals obtained by the same acoustic wave detecting device in different scan positions are added to obtain a summed signal for each acoustic wave detecting device. In a normalizing step, the summed signal is normalized for each scan position and for each acoustic wave detecting device to obtain a normalized signal. In a reducing step, a reduced signal for each acoustic wave detecting device in each scan position is obtained using the received signal and the normalized signal. Such processes can effectively reduce an amplitude caused by an interfacial acoustic wave and that caused by a reflected interfacial acoustic wave even when the spatial distribution of light intensity has a large difference in intensity.

The second embodiment will be described in detail with reference to FIGS. 10 and 11.

Configuration of Apparatus

Figure 10:
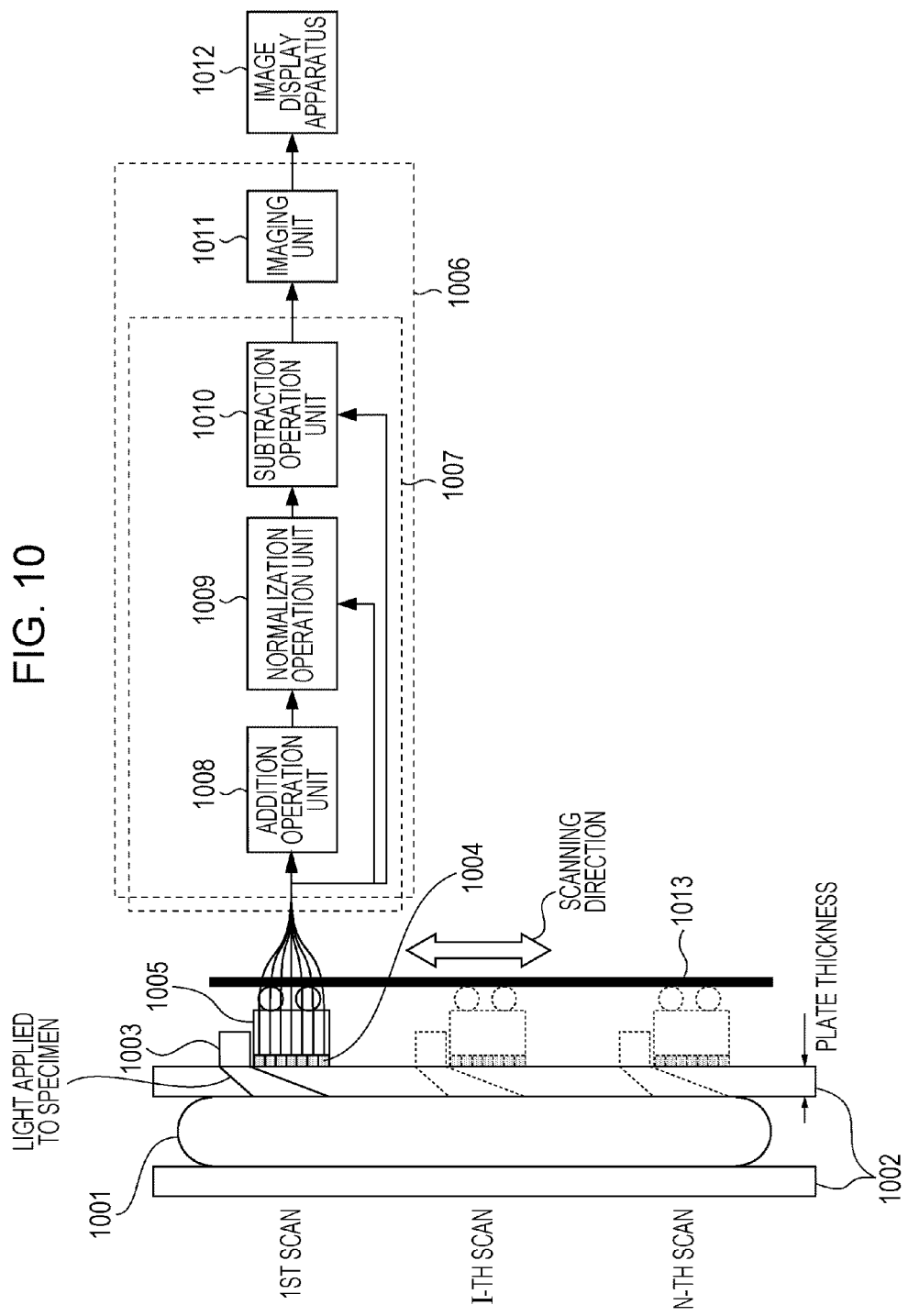
FIG. 10 is a schematic diagram illustrating a photoacoustic imaging apparatus according to a second embodiment.

FIG. 10 illustrates the configuration of the photoacoustic imaging apparatus according to the present embodiment. In the photoacoustic imaging apparatus according to this embodiment, light is emitted from a light source and a specimen 1001 is irradiated with the light through an irradiating unit 1003. A generated acoustic wave reaches acoustic wave detecting devices 1004 through a holding plate 1002. The acoustic wave detecting devices 1004 receive the acoustic wave, convert the wave into received signals, and output the signals to a signal processor 1006. The signal processor 1006 performs, for example, amplification and digital conversion on the received signals and then transmits the digitally converted received signals to an addition operation unit (adding unit) 1008. A signal output from the addition operation unit 1008 is supplied to a normalization operation unit (normalizing unit) 1009. Signals normalized by the normalization operation unit 1009 are supplied to a subtraction operation unit (reducing unit) 1010. The addition operation unit 1008, the normalization operation unit 1009, and the subtraction operation unit 1010 constitute an interfacial acoustic wave reducer 1007. The details of processes will be described later. Signals output from the interfacial acoustic wave reducer 1007 are supplied to an imaging unit 1011. The imaging unit 1011 generates image data using the supplied signals (image reconstruction). The generated image data is output to an image display apparatus 1012 and is then displayed as an image on the image display apparatus 1012. In the present embodiment, the photoacoustic imaging apparatus further includes, as a scanning unit scanning a light-irradiated area synchronously with the acoustic wave detecting devices, a scan mechanism 1013 that scans the acoustic wave detecting devices and the irradiating unit relative to a specimen. The scan mechanism 1013 can scan within the surface of the holding plate 1002 and is scanned simultaneously with the irradiating unit 1003 and the acoustic wave detecting devices 1004 (namely, a device array 1005). Specifically, when the device array 1005 is in any of positions for the first scan, the I-th scan, and the N-th scan illustrated in FIG. 10, the distribution of light intensity on the surface of the specimen as viewed from the device array 1005 is substantially the same on condition that a maximum light intensity is normalized to 1.

Although the present embodiment differs from the first embodiment in terms of the details of the processes in the interfacial acoustic wave reducer and the scanning unit, other components are the same as those in the first embodiment. Accordingly, explanation of the same components and terms is omitted.

Processes

Processes in the signal processor 1006 in FIG. 10 will be described with reference to FIG. 11. FIG. 11 is a flow diagram explaining a flow of signals when n acoustic wave detecting devices 1004 perform measurement N times while changing a scan position (i.e., at N scan positions). Let $p_i^I(t)$ denote a time-series received signal 1102 obtained by the i-th acoustic wave detecting device at the I-th scan position.

In the adding step by the addition operation unit 1008, received signals obtained by each acoustic wave detecting device in different scan positions are added at each time when elapsed times from the reference time of irradiation with light in the scan positions are equal. In other words, amplitude values in the received signals obtained by the same acoustic wave detecting device at each scan position are added at the same points in time. In FIG. 11, let $p_i^{SUM}(t)$ denote a summed signal obtained by adding the received signals output from the i-th acoustic wave detecting device in the N different scan positions.

The reason why received signals obtained by the same acoustic wave detecting device in different scan positions are added in the present embodiment will be described below. When the spatial distribution of intensity of light applied to a specimen has a large difference in intensity, the wave front of an interfacial acoustic wave is disturbed due to diffraction accompanying propagation (namely, the interfacial acoustic wave is not a plane wave). If the interfacial acoustic wave is multiply reflected inside a holding plate, the distance of propagation increases. Thus, the disturbance of the wave front further increases. Accordingly, as the number of reflection times of a reflected interfacial acoustic wave is larger, the disturbance of the wave front thereof gets larger. Therefore, the difference in the time of receiving the same interfacial acoustic wave between acoustic wave detecting devices increases. In this case, if received signals of acoustic wave detecting devices are added as in the first embodiment, amplitudes caused by a multiply reflected interfacial acoustic wave may not be added. Hence, the acoustic wave detecting devices and an irradiated area are scanned and received signals of each acoustic wave detecting device in different scan positions are added. Even if the scan positions are different, the distributions of light intensity on the surface of a specimen in front of the device array 1005 are substantially the same on condition that a maximum light intensity is normalized to 1. Consequently, an interfacial acoustic wave and a reflected interfacial acoustic wave reached the device array 1005 have substantially the same wave front shape. In other words, the times of receiving an interfacial acoustic wave and a reflected interfacial acoustic wave (or elapsed times from the time of irradiation with light to the time of reception) by the same acoustic wave detecting device in different positions are substantially identical with each other. Therefore, received signals of the same acoustic wave detecting device are added, so that amplitudes caused by an interfacial acoustic wave and a reflected interfacial acoustic wave are added. As for an acoustic wave generated from a light absorber, since the position of each acoustic wave detecting device 1004 relative to the light absorber varies depending on the scan position, the time of receiving the acoustic wave from the light absorber by the same acoustic wave detecting device 1004 varies depending on the scan position. Accordingly, when received signals of the same acoustic wave detecting device are added, amplitudes caused by the light absorber are not added.

A normalizing step in the normalization operation unit 1009 will be described below. In this step, the above-described summed signal for each acoustic wave detecting device is normalized for each scan position. In FIG. 11, let $A_i^{SUM}$ denote a maximum amplitude value included in the summed signal $p_i^{SUM}(t)$ for the i-th acoustic wave detecting device and let $A_i^I$ denote an amplitude value in the received signal $p_i^I(t)$ at the time when the maximum amplitude value $A_i^{SUM}$ is obtained. In the normalization operation unit 1009, the amplitude value $A_i^I$ in the received signal $p_i^I(t)$ obtained by the i-th acoustic wave detecting device in the I-th scan position at the time when the maximum amplitude value $A_i^{SUM}$ is obtained in the summed signal $p_i^{SUM}(t)$ for the i-th acoustic wave detecting device is used as a reference. The summed signal $p_i^{SUM}(t)$ for the acoustic wave detecting device is normalized for each scan position on the basis of the reference, thus obtaining a normalized signal $p_i^{I-SUM'}(t)$. Specifically, the summed signal $p_i^{SUM}(t)$ for the acoustic wave detecting device may be multiplied by a ratio of the amplitude value $A_i^I$ to the maximum amplitude value $A_i^{SUM}$, i.e., $A_i^I/A_i^{SUM}$.

The reason why the summed signal for each acoustic wave detecting device is normalized for each scan position will now be described. A light source of the photoacoustic imaging apparatus has to have such a light intensity that deep part of a specimen can be irradiated with light and generate pulsed light of several hundreds of nanoseconds or less. Accordingly, a pulse laser is generally used. Since such a pulse laser is typically large, it is difficult to scan the pulse laser itself relative to a specimen. In many cases, therefore, an optical system for spatially propagating laser light or a light guide member (which may also function as an irradiating unit), such as an optical fiber, is used to guide light emitted from the pulse laser to the vicinity of a specimen and the irradiating unit irradiates the specimen with light in each scan position. In the use of the light guide member and the irradiating unit, when the positions of acoustic wave detecting devices change due to scanning, the placement of the optical system is actively changed, alternatively, the shape of the fiber is passively changed in order to guide light to a scan position. When these changes occur, the intensity of light applied to the specimen may vary. As for a certain acoustic wave detecting device, if the position of the detecting device changes, the reception time (or the interval from the time of irradiation with light to the time of reception) of each of an interfacial acoustic wave and a reflected interfacial acoustic wave in one scan position is substantially identical to that in another scan position but an amplitude value caused by each of the interfacial acoustic wave and the reflected interfacial acoustic wave in a received signal in the one scan position differs from that in the other scan position because of a variation in light intensity caused by scanning.

Even when the summed signal for each acoustic wave detecting device is averaged, therefore, it is difficult to allow the amplitudes caused by the interfacial acoustic wave and the reflected interfacial acoustic wave in the summed signal to match those in the received signal. Accordingly, even when the averaged summed signal is subtracted from the received signal in the reducing step following the normalizing step, it is difficult to sufficiently reduce the interfacial acoustic wave and the reflected interfacial acoustic wave. According to the present embodiment, therefore, in the normalization operation unit 1009, the summed signal $p_i^{SUM}(t)$ for the i-th acoustic wave detecting device is multiplied by $A_i^I/A_i^{SUM}$ to allow an amplitude caused by each of the interfacial acoustic wave and the reflected interfacial acoustic wave to match the amplitude value $A_i^I$ in the received signal $p_i^I(t)$ obtained by the i-th acoustic wave detecting device in the I-th scan position.

The reducing step in the subtraction operation unit 1010 will now be described. In FIG. 11, a reduced signal $p_i^{I'}(t)$ is obtained using the received signal $p_i^I(t)$ and the normalized signal $p_i^{I-SUM'}(t)$. In the reduced signal, the amplitudes caused by the interfacial acoustic wave and the reflected interfacial acoustic wave are reduced. Specifically, the normalized signal $p_i^{I-SUM'}(t)$ is subtracted from the received signal $p_i^I(t)$. The amplitudes caused by the interfacial acoustic wave and the reflected interfacial acoustic wave in the normalized signal $p_i^{I-SUM'}(t)$ match those in the received signal $p_i^I(t)$ in value. Therefore, the above-described operation can reduce the amplitudes caused by the interfacial acoustic wave and the reflected interfacial acoustic wave (to zero in theory). On the other hand, an amplitude caused by a light absorber in the normalized signal is approximately zero. Accordingly, even when the normalized signal is subtracted from the received signal, the amplitude caused by the light absorber is hardly reduced.

Methods of obtaining a normalized signal and a reduced signal are not limited to the above-described operation methods. The summed signal $p_i^{SUM}(t)$ for each acoustic wave detecting device may be divided by the amplitude value $A_i^I$ to normalize the summed signal using the application of another normalization described in the first embodiment. In other words, so long as the summed signal for each acoustic wave detecting device can be normalized for each scan position, any operation method can be used. As for reduction, so long as amplitudes caused by the interfacial acoustic wave and the reflected interfacial acoustic wave are reduced using the normalized signal and the received signal, any operation method can be used.

Finally, the reduced signals are output to the imaging unit 1011. The imaging unit 1011 generates image data using the reduced signals. As described above, when the image data is generated using the reduced signals, artifacts caused by the interfacial acoustic wave and the reflected interfacial acoustic wave are reduced in an image as compared with a case where image data is directly generated from received signals (the present embodiment is not applied).

Third Embodiment

The present invention may be achieved by executing the following process. Specifically, in the process, software (program) for implementing the functions of the above-described first and second embodiments is supplied to a system or apparatus through a network or any of various storage media and, after that, a computer (or CPU or MPU) of the system or apparatus reads out and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-070326 filed Mar. 25, 2010, which is hereby incorporated by reference herein in its entirety.

What is claimed is:

1. An apparatus comprising:
a plurality of acoustic wave detecting devices configured to receive an acoustic wave generated in a specimen irradiated with light and convert the acoustic wave into a received signal, respectively; and
a signal processor configured to obtain image data using a plurality of received signals obtained by each of the acoustic wave detecting devices, wherein
the signal processor includes:
an adding unit configured to obtain a summed signal by adding amplitude values in the plurality of received signals obtained by the plurality of acoustic wave detecting devices;
a normalizing unit configured to obtain a normalized signal by normalizing the summed signal by using a maximum amplitude value in the summed signal and an amplitude value in the plurality of received signals at the time when the maximum amplitude value in the summed signal is obtained;
a reducing unit configured to obtain a plurality of reduced received signals by reducing amplitude values of the plurality of received signals by using the normalized signal; and
an imaging unit configured to obtain image data using the plurality of reduced received signals.

2. The apparatus according to claim 1, wherein
the normalizing unit is configured to obtain the normalized signal by using the summed signal and a ratio of the amplitude value in the plurality of received signals at the time when the maximum amplitude value in the summed signal is obtained to the maximum amplitude value in the summed signal.

3. An apparatus comprising:
an irradiating unit configured to irradiate a specimen with light emitted from a light source;
an acoustic wave detecting device configured to receive an acoustic wave generated in the specimen irradiated with the light and convert the acoustic wave into a received signal;
a scanning unit configured to scan the acoustic wave detecting device and the irradiating unit; and
a signal processor configured to obtain image data using a plurality of received signals obtained by the acoustic wave detecting device in each of scan positions, wherein
the light emitted from the light source is applied through the irradiating unit to the specimen in each scan position, and
the signal processor includes:
an adding unit configured to obtain a summed signal by adding amplitude values in the plurality of received signals;
a normalizing unit configured to obtain a normalized signal by normalizing the summed signal by using a maximum amplitude value in the summed signal and an amplitude value in the plurality of received signals at the time when the maximum amplitude value in the summed signal is obtained;
a reducing unit configured to obtain a plurality of reduced received signals by reducing amplitude values of the plurality of received signals by using the normalized signal; and
an imaging unit configured to obtain image data using the plurality of reduced received signals.

4. The apparatus according to claim 1, wherein
the normalizing unit configured to obtain a plurality of normalized signals corresponding to each of the plurality of received signals by normalizing the summed signal by using the maximum amplitude value in the summed signal and each of amplitude values in the plurality of received signals at the time when the maximum amplitude value in the summed signal is obtained, and
the reducing unit configured to obtain a plurality of reduced received signals by reducing amplitude values of the plurality of received signals by using the normalized signals corresponding to each of the plurality of received signals.

5. The apparatus according to claim 1, wherein
the reducing unit is configured to obtain the plurality of reduced received signals by obtaining a difference between the plurality of received signals and the normalized signal.

6. The apparatus according to claim 3, wherein
the normalizing unit is configured to obtain the normalized signal by using the summed signal and a ratio of the amplitude value in the plurality of received signals at the time when the maximum amplitude value in the summed signal is obtained to the maximum amplitude value in the summed signal.

7. The apparatus according to claim 3, wherein
the reducing unit is configured to obtain the plurality of reduced received signals by obtaining a difference between the plurality of received signals and the normalized signal.

8. An apparatus comprising:
an irradiating unit configured to irradiate a specimen with light emitted from a light source;
a plurality of acoustic wave detecting devices configured to receive an acoustic wave generated in the specimen irradiated with the light and convert the acoustic wave into the received signal, respectively;

a scanning unit configured to scan the plurality of acoustic wave detecting devices and the irradiating unit; and a signal processor configured to obtain image data by using a plurality of received signals obtained by the acoustic wave detecting devices in each of scan positions, wherein the signal processor includes:
- an adding unit configured to obtain summed signals corresponding to each of the plurality of acoustic wave detecting devices by adding amplitude values in the plurality of received signals obtained by one of the plurality of acoustic wave detecting devices in each of the scan positions,
- a normalizing unit configured to obtain normalized signals corresponding to the plurality of acoustic wave detecting devices by normalizing the summed signals by using maximum amplitude values in each of the summed signals and amplitude values in each of the plurality of received signals obtained by the one of the plurality of acoustic wave detecting devices in each of the scan positions at the time when each of the maximum amplitude values in the summed signals is obtained;
- a reducing unit configured to obtain a plurality of reduced received signals by reducing amplitude values of the plurality of received signals obtained by each of the plurality of acoustic wave detecting devices by using the normalized signals corresponding to each of the plurality of acoustic wave detecting devices; and
- an imaging unit configured to obtain the image data using the plurality of reduced received signals.

9. An apparatus comprising:
a plurality of acoustic wave detecting devices configured to receive an acoustic wave generated by irradiating a specimen with light and convert the acoustic wave into a time-series received signal, respectively; and a signal processor configured to obtain information on an interior of the specimen using a plurality of time-series received signals obtained by each of the acoustic wave detecting devices, wherein the signal processor is configured to reduce amplitude values of substantially temporally identical signals included within the plurality of time-series received signals and obtain the information using the plurality of time-series received signals among which the amplitude values of the substantially temporally identical signals are reduced.

10. An apparatus comprising:
a plurality of acoustic wave detecting devices configured to receive an acoustic wave generated by irradiating a specimen with light and convert the acoustic wave into a time-series received signal, respectively; and a signal processor configured to obtain information on an interior of the specimen using a plurality of time-series received signals obtained by each of the acoustic wave detecting devices, wherein the signal processor is configured to reduce amplitude values of signals that are caused by an interfacial acoustic wave and are included in the plurality of time-series received signals and obtain the information using the plurality of time-series received signals among which the amplitude values of the signals caused by the interfacial acoustic wave are reduced.

11. An apparatus comprising:
a plurality of acoustic wave detecting devices configured to receive an acoustic wave generated by irradiating a specimen with light and convert the acoustic wave into a time-series received signal, respectively; and a signal processor configured to obtain information on an interior of the specimen using a plurality of time-series received signals obtained by each of the acoustic wave detecting devices, wherein the signal processor is configured to reduce amplitude values of signals that are caused by a reflected interfacial acoustic wave and are included in the plurality of time-series received signals and obtain the information by using the plurality of time-series received signals among which the amplitude values of the signals caused by the reflected interfacial acoustic wave are reduced.

12. The apparatus according to claim 10, wherein
the interfacial acoustic wave is an acoustic wave generated on a surface of the specimen irradiated with light.

13. The apparatus according to claim 10, wherein
the interfacial acoustic wave is an acoustic wave generated on a surface of the plurality of acoustic wave detecting devices irradiated with light.

14. The apparatus according to claim 11, wherein
the reflected interfacial acoustic wave is a reflected wave of an acoustic wave generated on a surface of the specimen irradiated with light.

15. The apparatus according to claim 11, wherein
the reflected interfacial acoustic wave is a reflected wave of an acoustic wave generated on a surface of the plurality of acoustic wave detecting devices irradiated with light.

* * * * *